United States Patent [19]

Mackles et al.

[11] Patent Number: 4,999,183

[45] Date of Patent: Mar. 12, 1991

[54] SHAVING COMPOSITIONS

[76] Inventors: Leonard Mackles, 311 E. 23rd St., New York, N.Y. 10010; Leonard Chavkin, R.R. 1, Box 90, Bloomsbury, N.J. 08804

[21] Appl. No.: 415,574

[22] Filed: Oct. 2, 1989

[51] Int. Cl.$^5$ ................................................. A61K 7/00
[52] U.S. Cl. ......................................... 424/47; 424/45; 424/70; 424/73; 424/78
[58] Field of Search ................. 424/45, 47, 70, 73, 424/78

[56] References Cited

U.S. PATENT DOCUMENTS

| | | | |
|---|---|---|---|
| 3,923,970 | 12/1975 | Breuer | 424/47 |
| 4,075,318 | 2/1978 | Kelly et al. | 424/70 |
| 4,076,799 | 2/1978 | Willer et al. | 424/45 |
| 4,445,521 | 5/1984 | Grollier et al. | 424/47 |
| 4,478,853 | 10/1984 | Chaussee | 424/70 |
| 4,661,340 | 4/1987 | Nagy née Kricsfalussy et al. | 424/47 |
| 4,752,465 | 6/1988 | Mackles | 424/45 |

*Primary Examiner*—Merrell C. Cashion, Jr.
*Assistant Examiner*—P. L. Prater

[57] ABSTRACT

There is provided a shaving facilitator comprising a composition of pH 5.0–10.0, compounded from a polyethylene oxide polymer (PEOP) a polysulfonic acid polymer (PSAP) and a topically acceptable base. The shaving of hirsute areas of skin is facilitated by applying such a composition to said areas prior to the application of a shaving soap product thereto. Additionally this polymer composition can be incorporated in other, conventional shaving products such as lotions for women's legs and underarms or in aerosol shave foam for use by men and women.

24 Claims, No Drawings

SHAVING COMPOSITIONS

BACKGROUND OF THE INVENTION

1. Field of the Invention

Provision of novel composition to facilitate the shaving of body hair.

2. Discussion of the Prior Art

The active ingredient in products that are used for wet shaving by men is a soap. The procedure that is most satisfactory involves washing the face with bar soap and leaving it wet and soapy. Then a shaving product is applied which softens the beard and provides lubricity to permit the razor to glide across the face removing the beard with minimal scraping of the skin.

Soap is the ideal single ingredient for this purpose and is most widely used in shaving products. Its alkalinity causes the beard to hydrate and soften to facilitate its removal. In the process the outer cuticle of the hair opens to allow it to be more easily cut by the blade. In addition, the soap causes the keratin layer of the skin to hydrate to minimize the drag of the blade during its passage across the skin thus minimizing irritation and cutting of the skin.

Soap used alone, however, is not perfect. Soap lather dries too quickly on the face—so quickly that if soap alone is used as with a shaving mug and brush—the lather must be worked up and re-applied several times during the course of a single shaving procedure.

In addition most men find shaving with soapy to be too irritating. Younger men, particularly with sensitive skin in the neck area, experience irritation and rashes when shaving with soap alone. Since acne pustules are also commonly present in this age group, cuts are common incident to shaving.

During the past decades many approaches have been taken in products formulated to improve blade shaving with soap. Brushless shaving creams were developed which were more emollient and lubricious than soap alone due to the fats and waxes they contained. Typically stearic acid and fatty alcohols were used to provide added lubrication and to prevent drying out on the face. These did a poor job of hydrating the beard and skin, so a close shave was impossible. Additionally, the added fats and waxes made rinsing the razor very difficult and prolonged the shaving process measurably. As a result these products fell into disuse.

The advent of the aerosol foam shaves quickly replaced other products that delivered soap to the face because of their convenience. They still suffered from the disadvantages of soap as the single active shaving ingredient and formulation efforts continued in order to make the aerosol shaving products more effective and more comfortable.

It is possible to add humectants and emollients to the aqueous soap solutions typical of foam shaves and these are commonly used by the formulators skilled in the art of preparing such products. Glycerin, propylene glycol, sorbitol as humectants and lanolin, fatty alcohols, esters and ethers and other fatty vegetable animal and mineral oils commonly appear in these formulations.

None of these go far enough in improving the performance of the basic soap solution of foam shaves to make the product demonstrably superior to the user. Additionally many of these materials reduce the performance of the soap by an antifoam effect or make the product more difficult to rinse from the razor as a result of their lipophilic nature.

More recently water soluble polymers have been employed experimentally in shaving products since they impart lubricity to aqueous solutions. However, it has been found that they lose their discernible lubricity in the presence of soap and worse still, they develop an unpleasant stringiness in combination with soap.

The way those skilled in the art have attempted to cope with the problem is by applying these polymers separately. Currently the major razor manufacturers are marketing razors with solid strips of these polymers bonded to the shaving surface of the razor above the blades. Most of these use a strip of high molecular weight polymers of ethylene oxide, commercially known as Polyox resin (manufactured by Union Carbide Corp.).

These poly (ethylene oxide) polymers bonded to the razor soon become inoperative due to their interaction with the shaving cream soap. It would be desireable to utilize the outstanding slip characteristic of these polyethylene oxide polymers when in contact with soap solutions such as found in shaving creams, without the polyethylene polymer becoming stringy and unusable.

It is known that polyethylene oxide polymers have strong hydrogen bonding properties that account for the association of these polyethers with various polar compounds. These novel complexes can be discrete chemical entities resulting from very strong intermolecular association and often exhibit properties markedly different from either component.

SUMMARY

There is provided a shaving facilitator comprising a composition of pH 5.0–10.0, compounded from a polyethylene oxide polymer (PEOP) of molecular weight between 0.5 and 5 million, suitably about 1 to 2 million, a polysulfonic acid polymer (PSAP) of molecular weight between 100,000 to 500,000, suitably about 300,000 and a topically acceptable base, wherein the ratio of PEOP to PSAP is from about 3:1 to about 1:10 and sufficient base is utilized to adjust the pH of the mixture of the polymers to the desired range.

The composition is suitably formulated as a gel, preferably an aqueous gel whose consistency may vary from substantially liquid to substantially solid.

The composition is made by dissolving the PEOP in a suitable solvent, such as water, adding the PSAP and then adding the base until the desired pH is obtained.

The composition can be used for facilitating shaving of hirsute areas of skin by applying it to said areas prior to the application of shaving soap thereto, followed by the conventional application of a razor. The composition, when mixed with a standard aerosol foam shave on the face does not result in stringiness or pituitousness and an amazingly smooth, lubricious shave is obtained. The results, in terms of lubriciousness, are superior to those obtained when either polymer is used alone.

This combination of polymers, when applied to the beard prior to the application of a foam shave or soap gel give a superior smooth comfortable shave without razor irritation and with no pituitousness. It allows rapid shaving without nicks or cuts. It lubricates the razor and increases the useful life of the cutting edges.

This composition can be used as such in gel or lotion form as a pre-shave or shaving product. It can also be incorporated into an oil-in-water emulsion lotion for use as a single shaving product by women. Similarly, it can be incorporated into a conventional soap based aerosol foam shave formulation for use by men or women as a single shaving product.

Thus, it is possible to use the basic two polymer combination composition in preparing any of the following product forms:
1. Preshave gel for men for beard shaving.
2. Preshave or Shaving Lotion for women's legs and underarms.
3. Aerosol foam shave for men or women.

In all these products the fragrances, preservatives, colors normally used in such products for cosmentic purposes can be incorporated.

DESCRIPTION OF THE PREFERRED EMBODIMENTS

The shaving facilitator is a material intended for the treatment of facial or body hair prior to or concurrent with the application of shaving soap to permit a smoother shave with reduced levels of skin abrasion. It comprises a composition of pH 5.0–10.0, preferably 6.5–8, compounded from a polyethylene oxide polymer (PEOP) of molecular weight between 0.5 and 5 million, suitably about 1 to 2 million, a polysulfonic acid polymer (PSAP) of molecular weight between 100,000 and 500,000, suitably about 300,000 and a topically acceptable base, wherein the ratio of PEOP to PSAP is from about 3:1 to about 1:10 preferably about 1:1 and sufficient base is utilized to adjust the pH of the mixture of the polymers to the desired range.

Any PSAP may be utilized, among the general categories may be mentioned polyacrylamidoalkane sulfonic acids such as subpoly N-acryloyl taurine and polymethacryloyl taurine preferrably polyacrylamidomethylpropane sulfonic acid. This latter is commercially available as Polymer HSP 1180 from Henkel Corp (Hoboken, N.J.). This product is supplied as a 15% w/v aqueous solution of pH 2.0. However it is generally used as a salt resulting from neutralization with a base to pH 5.0–9.0.

Any topically acceptable base may be employed. Inorganic bases such as sodium or potassium hydroxides or organic bases such as mono, di or triethanolamine can be used.

It will be understood by those skilled in the art that in order to achieve the desired consistencies of the various embodiments of this invention variations in the formulations are required.

The preshave gels comprise (percentage by weight, based on total weight of final product) a total of PEOP/PSAP of 0.5 to 6.0, suitably 3–4%, glycerin: 1.0–10.0%, suitably about 5%, water: 80.0–95.0%, suitably about 90%, and, when employed, Carbomer 940:0.1 to 1.0, suitably about 0.5%. The amount of base added should bring the composition to a pH of about 5 to about 10, suitably about pH 7–8.

The shave gels formulated for use by women, that is to say especially for leg and underarm use, rather than facial beard use, comprise (percentage by weight, based on total weight of final product) a total of PEOP/PSAP of 0.5 to 2.0, suitably about 1%, fatty acid ($C_{12}$–$C_{14}$): 2.0–10.0% and water: 75.0–90.0%, suitably about 85%. The amount of base added should bring the composition to a pH of about 5 to about 10, suitably about pH 8–9.

While the formulations of the present invention are most effective when used as preshave gels, it is recognised that certain users may prefer a unitary formulation including a foam. Thus there may be provided aerosol shave creme formulations which comprise (percentage by weight, based on total weight of final product) a total of PEOP/PSAP of 0.5 to 2.0, suitably about 1%, fatty acid ($C_{12}$–$C_{14}$): 2.0–10.0%, suitably about 5%, glycerin: 2.0–10.0%, suitably about 5%, water: 65.0–85.0%, suitably about 77%, emollients: 1.5 to 7.0, suitably about 4% and propellants: 2.0–5.0, suitably about 4%. The amount of base added should bring the composition to a pH of about 5 to about 10, suitably about pH 9. Any emollients or propellants conventionally used in aerosol shave foams may be employed.

EXAMPLES

| EXAMPLE #1 PRESHAVE GEL | |
|---|---|
| | % |
| Polysulfonic Acid polymer (HSP-1180) 15% Active | 20.00 |
| Polyethylene oxide polymer (Polyox WSRN-60K) MW 2,000,000 | 1.00 |
| Triethanolamine, (TEA) 98% | 5.00 |
| Glycerin | 5.00 |
| Water | 69.00 |
| | 100.00 |

The Polyox is dissolved in the water and glycerin. The HSP-1180 is added with stirring till the system is clear and uniform. The TEA is added with good mixing, till clear and uniform. Ratio of PEOP to PSAP = 1:3

This composition can be filled into tubes and marketed as such.

| EXAMPLE #2 PRESHAVE GEL | |
|---|---|
| | % |
| Polysulfonic Acid Polymer (HSP-1180) 15% Active | 14.00 |
| Polyethylene Oxide Polymer (Polyox WSRN-12K) M.W. 1,000,000 | 2.00 |
| Glycerin | 5.00 |
| Triethanolamine (98%) | 4.00 |
| Water | 75.00 |
| | 100.00 |
| Ratio of PEOP to PSAP = 1:1 | |

The Polyox is dissolved in the water and glycerin. The HSP-1180 is added with stirring till the system is clear and uniform. The TEA is added with good mixing till clear and uniform.

| EXAMPLE #3 PRESHAVE GEL-STIFF GEL | |
|---|---|
| | % |
| Polysulfonic Acid polymer (HSP-1180) 15% Active | 14.00 |
| Polyethylene oxide polymer (Polyox WSRN-12K) M.W. 1,000,000 | 2.00 |
| CARBOMER 940 (Carbopol 940) B. F. Goodrich* | 0.50 |
| Triethanolamine 98% | 6.00 |
| Glycerin | 5.00 |
| Water | 72.50 |
| | 100.00 |
| Ratio PEOP to PSAP = 1:1 | |

*Carbomer 940 Crosslinked polyacrylic acid polymer.

The Polyox and Carbomer 940 are dissolved in the water and glycerin. The HSP-1180 is added with stirring till the system is clear and uniform. The TEA is added with good mixing till clear and uniform.

EXAMPLE #4 PRESHAVE GEL-Using NaOH for Neutralization

| | % |
|---|---|
| Polysulfonic Acid Polymer (HSP-1180) 15% Active | 14.00 |
| Polyethylene Oxide Polymer (Polyox WSRN-12K) M.W. 1,000,000 | 2.00 |
| Glycerin | 5.00 |
| Sodium Hydroxide | 1.00 |
| Water | 78.00 |
| | 100.00 |

Ratio PEOP to PSAP = 1:1

The Polyox is dissolved in 90% of the water and glycerin. The HSP-1180 is added with stirring till the system is clear and uniform. The sodium hydroxide is dissolved in the 10% water held out. When the base is fully dissolved the solution is added to the batch with good mixing till clear and uniform.

EXAMPLE #5 WOMAN'S SHAVE LOTION
Preshave or Shave Lotion

| | % |
|---|---|
| Polysulfonic Acid Polymer (HSP-1180) 15% Active | 3.00 |
| Polyethylene Oxide Polymer (Polyox WSRN-12K) M.W. 1,000,000 | 0.05 |
| Triethanolamine | 7.00 |
| Stearic Acid T.P. | 2.50 |
| Stripped Coconut Fatty Acid | 2.50 |
| Cetyl Alcohol | 2.00 |
| Water | 82.50 |
| | 100.00 |

Ratio PEOP to PSAP = 1:1

The Polyox is dissolved in the water. The HSP-1180 is added with stirring till the system is clear and uniform. The TEA is added with good mixing. Heat is applied and the temperature brought to 60° C. In another vessel the stearic acid, coconut fatty acid, and cetyl alcohol are heated to 60° C. The oil phase is now added to the heated water phase with good agitation. The batch is then cooled to ambient temperature.

EXAMPLE #6 AEROSOL SHAVE CREAM

| | % |
|---|---|
| Polysulfonic Acid Polymer (HSP-1180) 15% Active | 3.00 |
| Polyethylene Oxide Polymer (Polyox WSRN-12K) M.W. 1,000,000 | 0.50 |
| Triethanolamine | 3.00 |
| Stearic Acid T.P. | 3.00 |
| Cetyl Alcohol | 1.00 |
| Acetulan (Acetylated lanolin alcohols) | 3.00 |
| Glycerin | 5.00 |
| Water | 77.50 |
| Propellant A 46 (Isobutane/propane mixture) | 4.00 |
| | 100.00 |

Ratio PEOP to PSAP = 1:1

The Polyox is dissolved in the water and glycerin. The HSP-1180 is added with stirring till the system is clear and uniform. The TEA is added with good mixing and the batch temperature is brought to 60° C. In another vessel the stearic acid, cetyl alcohol and Acetulan are heated to 60° C. The oil phase is added to the water with good agitation and the batch cooled to ambient temperature. Batch is delivered for aerosol filling.

We claim:

1. A shaving facilitator comprising a composition of pH 5.0–10.0, compounded from: a polyethylene oxide polymer (PEOP) of molecular weight between 0.5 and 5 million, a polysulfonic acid polymer (PSAP) of molecular weight between 100,000 and 500,000, wherein said polysulfonic acid polymer is selected from the group consisting of polyacrylamidoalkane sulfonic acids, and a topically acceptable base, wherein the ratio of PEOP to PSAP is from about 3:1 to about 1:10 and sufficient base is utilized to adjust the pH of the mixture of the polymers to within the range of 5.0–10.0.

2. A composition of claim 1 the PEOP:PSAP ratio is from about 2:1 to about 1:3.

3. A composition of claim 2 wherein the base is an organic or inorganic base.

4. A composition of claim 3 wherein the base is triethanolamine.

5. A composition of claim 3 wherein the base is an alkali metal hydroxide.

6. A composition of claim 5 wherein the base is sodium or potassium hydroxide.

7. A composition of claim 1 wherein the PSAP is poly N-acryloyl taurine and poly methacryloyl taurine.

8. A composition of claim 7 wherein the PSAP is polyacrylamidomethylpropane sulfonic acid.

9. A composition of claim 7 wherein the PEOP has an M.W of about 1,000,000 the PSAP is polyacrylamidomethyl-propane sulfonic acid and has an M.W. of about 300,000, the base is triethanolamine, the pH is 6.5–8, and the PEOP:PSAP ratio is about 1:1.

10. A composition of claim 2 in gel form.

11. A composition of claim 10 in gel form further comprising water and glycerin.

12. A composition of claim 10 comprising:

| PEOP/PSAP | 0.5–6.0%, |
|---|---|
| Glycerin | 1.0–10.0%, |
| Water | 80.0–95.0%, |
| Base to | pH 7–8. |

13. A composition of claim 12 comprising:

| PEOP/PSAP | 3.0–4.0%, |
|---|---|
| Glycerin | about 5%, |
| Water | about 90%, |
| Base to | pH 7–8. |

14. A composition of claim 10 comprising:

| PEOP/PSAP | 0.5–2.0%, |
|---|---|
| Fatty Acid ($C_6$–$C_{12}$) | 2.0–10.0%, |
| Water | 75.0–90.0%, |
| Base to | pH 8–9. |

15. A composition of claim 10 comprising:

| PEOP/PSAP | about 1.0%, |
|---|---|
| Fatty Acid ($C_6$–$C_{12}$) | about 5%, |
| Water | about 85%, |
| Base to | pH 8–9. |

16. An aerosol foamable composition of claim 2 comprising:

| PEOP/PSAP | 0.5–2.0% |
|---|---|
| Glycerin | 2.0–10.0%, |
| Emollients | 1.5–7.0%, |

-continued

| | |
|---|---|
| Propellants | 2.0–5.0%, |
| Water | 65.0–85.0%, |
| Base to | about pH 9. |

17. An aerosol foamable composition of claim 16 comprising:

| | |
|---|---|
| PEOP/PSAP | about 1%, |
| Glycerin | about 5%, |
| Emollients | about 4%, |
| Water | about 77%, |
| Base to | about pH 9. |

18. A method of making an aqueous composition of the material of claim 1 which comprises
   (a) dissolving the PEOP in water,
   (b) adding the PSAP, and then adding the base until the desired pH is obtained.

19. A method of facilitating shaving of hirsute areas of skin which comprises applying a composition of claim 1 to said areas prior to the application of shaving soap thereto.

20. A method of facilitating shaving of hirsute areas of skin which comprises applying a composition of claim 11 to said areas prior to the application of shaving soap thereto.

21. A method of facilitating shaving of hirsute areas of skin which comprises applying a composition of claim 1 to said areas contemporaneously with the application of shaving soap thereto.

22. A method of facilitating shaving of hirsute areas of skin which comprises applying a composition of claim 11 to said areas contemporaneously with the application of shaving soap thereto.

23. A method of facilitating shaving of hirsute areas of skin which comprises applying a composition of claim 16 to said areas.

24. A method of facilitating shaving of hirsute areas of skin which comprises applying a composition of claim 17 to said areas.

* * * * *

UNITED STATES PATENT AND TRADEMARK OFFICE
CERTIFICATE OF CORRECTION

PATENT NO. : 4,999,183

DATED : March 12, 1991

INVENTOR(S) : Leonard Mackles and Leonard Chavkin

It is certified that error appears in the above-identified patent and that said Letters Patent is hereby corrected as shown below:

Example 5, Column 5, line 26,
Polyethylene Oxide Polymer should read 0.5%

Signed and Sealed this

Eleventh Day of August, 1992

Attest:

DOUGLAS B. COMER

Attesting Officer

Acting Commissioner of Patents and Trademarks